US008187252B2

(12) United States Patent
Buckley et al.

(10) Patent No.: US 8,187,252 B2
(45) Date of Patent: May 29, 2012

(54) SHAPE MEMORY SYSTEM WITH INTEGRATED ACTUATION USING EMBEDDED PARTICLES

(75) Inventors: Patrick R. Buckley, New York, NY (US); Duncan J. Maitland, Pleasant Hill, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 350 days.

(21) Appl. No.: 12/536,670

(22) Filed: Aug. 6, 2009

(65) Prior Publication Data

US 2009/0299335 A1 Dec. 3, 2009

Related U.S. Application Data

(62) Division of application No. 10/810,422, filed on Mar. 26, 2004, now Pat. No. 7,591,834.

(51) Int. Cl.
*A61M 31/00* (2006.01)
(52) U.S. Cl. ............................................. 604/508
(58) Field of Classification Search .................. 604/508
See application file for complete search history.

(56) References Cited

U.S. PATENT DOCUMENTS

| | | | |
|---|---|---|---|
| 5,330,483 A | 7/1994 | Heaven et al. | |
| 5,429,583 A * | 7/1995 | Paulus et al. ...................... | 600/2 |
| 5,674,242 A | 10/1997 | Phan et al. | |
| 5,762,630 A | 6/1998 | Bley et al. | |
| 5,895,398 A | 4/1999 | Wensel et al. | |
| 5,911,737 A | 6/1999 | Lee et al. | |
| 5,957,966 A | 9/1999 | Schroeppel et al. | |
| 5,964,744 A | 10/1999 | Balbierz et al. | |
| 6,059,815 A | 5/2000 | Lee et al. | |
| 6,090,072 A | 7/2000 | Kratoska et al. | |
| 6,102,917 A | 8/2000 | Maitland et al. | |
| 6,599,234 B1 | 7/2003 | Gray et al. | |
| 7,530,975 B2 * | 5/2009 | Hunter .......................... | 604/500 |
| 2002/0095169 A1 * | 7/2002 | Maitland et al. .............. | 606/194 |
| 2002/0113066 A1 * | 8/2002 | Stark et al. ..................... | 219/634 |
| 2006/0260534 A1 * | 11/2006 | Petrakis ........................ | 116/216 |

OTHER PUBLICATIONS

Cetas, T.C., et al., "A Ferrite Core/Metallic Sheath Thermoseed for Interstitial Thermal Therapies," IEEE Transactions on Biomedical Engineering, vol. 45, No. 1, Jan. 1998, pp. 68-77.
Oleson, James R., "A Review of Magnetic Induction Methods for Hyperthermia Treatment of Cancer," IEEE Transactions on Biomedical Engineering, vol. BME-31, No. 1, Jan. 1984, pp. 91-97.

(Continued)

*Primary Examiner* — Nicholas Lucchesi
*Assistant Examiner* — Jason Flick
(74) *Attorney, Agent, or Firm* — Eddie E. Scott (57) ABSTRACT

A shape memory material with integrated actuation using embedded particles. One embodiment provides a shape memory material apparatus comprising a shape memory material body and magnetic pieces in the shape memory material body. Another embodiment provides a method of actuating a device to perform an activity on a subject comprising the steps of positioning a shape memory material body in a desired position with regard to the subject, the shape memory material body capable of being formed in a specific primary shape, reformed into a secondary stable shape, and controllably actuated to recover the specific primary shape; including pieces in the shape memory material body; and actuating the shape memory material body using the pieces causing the shape memory material body to be controllably actuated to recover the specific primary shape and perform the activity on the subject.

34 Claims, 4 Drawing Sheets

OTHER PUBLICATIONS

Sato, M., et al., "An Experimental Study on a Soft Heating Method for Clinical Application of Interstitial Hyperthermia," IEEE Transactions on Magnetics, vol. 29, No. 6, Nov. 1993, pp. 3331-3333.

Jojo, M., et al., "Consideration of Handy Excitation Apparatus for the Inductive Hyperthermia," IEEE Transactions on Magnetics, vol. 37, No. 4, Jul. 2001, pp. 2944-2946.

Paulus, J.A., et al., "Evaluation of Inductively Heated Ferromagnetic Alloy Implants for Thereapeutic Interstitial Hyperthermia," IEEE Transactions on Biomedical Engineering, vol. 43, No. 4, Apr. 1996, pp. 406-413.

Wetzel, E., et al., "Feasibility of Magnetic Particle Films for Curie Temperature-Controlled Processing of Composite Materials," Army Research Laboratory, ARL-TR-2431, Mar. 2001, 58 pages.

McCurrie, R.A., "Ferromagnetic Materials Structure and Properties," Academic Press, Longon, 1994, 4 pages.

Jordan, J., et al., "Inductive Heating of Ferrimagnetic Particles and Magnetic Fluids: Physical Evaluation of Their Potential for Hyperthermia," Int. J. Hyperthermia, vol. 9, No. 1, 1993, pp. 51-68.

Matsuki, H., et al., "High Quality Soft Heating Method Utilizing Temperature Dependence of Permeability and Core Loss of Low Curie Temperature Ferrite," IEEE Transactions on Magnetics, vol. MAG-21, No. 5, Sep. 1985, pp. 1927-1929.

Stauffer, P. R., "Observations on the Use of Ferromagnetic Implants for Inducing Hyperthermia," IEEE Transactions on Biomedical Engineering, vol. BME-31, No. 1, Jan. 1984, pp. 76-90.

Hergt, R., et al., Physical Limits of Hyperthermia Using Magnetite Fine Particles, IEEE Transactions on Magnetics, vol. 34, No. 5, Sep. 1998, pp. 3745-3754.

Stauffer, P. R., "Practical Induction Heating Coil Designs for Clinical Hyperthermia with Ferromagnetic Implants," IEEE Transactions on Biomedical Engineering, vol. 41, No. 1, Jan. 1994, pp. 17-28.

Irie, M., "Shape Memory Polymers" (Chapter 9) from book "Shape Memory Materials," Cambridge University Press, United Kingdom, 1998, 19 pages.

Atkinson, W. J., et al., "Usable Frequencies in Hyperthermia with Thermal Seeds," IEEE Transactions on Biomedical Engineering, vol. BME-31, No. 1, Jan. 1984, pp. 70-75.

Kimura, I., et al., "VLF Induction Heating for Clinical Hyperthermia," IEEE Transactions on Magnetics, vol. MAG-22, No. 6, Nov. 1986, pp. 1897-1900.

* cited by examiner

FIG. 9

SHAPE MEMORY SYSTEM WITH INTEGRATED ACTUATION USING EMBEDDED PARTICLES

This application is a divisional of application Ser. No. 10/810,422 filed Mar. 26, 2004 now U.S. Pat. No. 7,591,834.

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to shape memory system and more particularly to a shape memory system using a shape memory material with integrated actuation using embedded particles.

2. State of Technology

U.S. Pat. No. 5,895,398 to Jeffrey P. Wensel and Y. Pierre Gobin for a method of using a clot capture coil, issued Apr. 20, 1999, provides the following state of technology information, "A clot and foreign body removal device is described which comprises a catheter with at least one lumen. Located within the catheter is a clot capture coil that is connected to an insertion mandrel. In one embodiment, the clot capture coil is made out of a solid elastic or superelastic material which has shape memory, preferably nitinol. The elasticity or superelasticity of the coil allows it to be deformed within the catheter and to then reform its original coil configuration when the coil is moved outside of the catheter lumen. In another embodiment the coil is a biphasic coil which changes shape upon heating or passing an electric current. Once the coil configuration has been established, the coil can be used to ensnare and corkscrew a clot in a vessel. A clot is extracted from the vessel by moving the clot capture coil and catheter proximally until the clot can be removed or released into a different vessel that does not perfuse a critical organ. Foreign bodies are similarly captured by deploying the coil distal to the foreign body and moving the clot capture coil proximally until the foreign body is trapped within the coil. By removing the device from the body, the foreign material is also removed." (Abstract)

U.S. Pat. No. 5,911,737 to Abraham P. Lee, M. Allen Northrup, Dino R. Ciarlo, Peter A. Krulevitch, and William J. Benett for microfabricated therapeutic actuators, issued Jun. 15, 1999 provides the following state of technology information, "Microfabricated therapeutic actuators are fabricated using a shape memory polymer (SMP), a polyurethane-based material that undergoes a phase transformation at a specified temperature (Tg). At a temperature above temperature Tg material is soft and can be easily reshaped into another configuration. As the temperature is lowered below temperature Tg the new shape is fixed and locked in as long as the material stays below temperature Tg. Upon reheating the material to a temperature above Tg, the material will return to its original shape. By the use of such SMP material, SMP microtubing can be used as a release actuator for the delivery of embolic coils through catheters into aneurysms, for example. The microtubing can be manufactured in various sizes and the phase change temperature Tg is determinate for an intended temperature target and intended use." (Abstract)

U.S. Pat. No. 6,059,815 to Abraham P. Lee, Joseph P. Fitch, Daniel L. Schumann, Luiz Da Silva, William J. Benett, and Peter A. Krulevitch, issued May 9, 2000, provides the following state of technology information, "Microfabricated therapeutic actuators are fabricated using a shape memory polymer (SMP), a polyurethane-based material that undergoes a phase transformation at a specified temperature (Tg). At a temperature above temperature Tg material is soft and can be easily reshaped into another configuration. As the temperature is lowered below temperature Tg the new shape is fixed and locked in as long as the material stays below temperature Tg. Upon reheating the material to a temperature above Tg, the material will return to its original shape. By the use of such SMP material, SMP microtubing can be used as a retaining/release actuator for the delivery of material, such as embolic coils, for example, through catheters into aneurysms, for example. The microtubing can be manufactured in various sizes and the phase change temperature Tg is determinate for an intended temperature target and intended use. The SMP microtubing can be positioned around or within an end of a deposit material. Various heating arrangements can be utilized with the SMP release mechanism, and the SMP microtubing can include a metallic coating for enhanced light absorption." (Abstract)

U.S. Pat. No. 6,102,917 to Duncan J. Maitland, Abraham P. Lee, Daniel L. Schumann, and Luiz Da Silva, issued Aug. 15, 2000, provides the following state of technology information, "A system for releasing a target material, such as an embolic coil from an SMP located at the end of a catheter utilizing an optical arrangement for releasing the material. The system includes a laser, laser driver, display panel, photodetector, fiber optics coupler, fiber optics and connectors, a catheter, and an SMP-based gripper, and includes a release sensing and feedback arrangement. The SMP-based gripper is heated via laser light through an optic fiber causing the gripper to release a target material (e.g., embolic coil for therapeutic treatment of aneurysms). Various embodiments are provided for coupling the laser light into the SMP, which includes specific positioning of the coils, removal of the fiber cladding adjacent the coil a metal coating on the SMP, doping the SMP with a gradient absorbing dye, tapering the fiber optic end, coating the SMP with low refractive index material and locating an insert between the fiber optic and the coil." (Abstract)

United States Patent Application No. 2002/0095169 by Duncan J. Maitland, Abraham P. Lee, Daniel L. Schumann, Dennis L. Matthews, Derek E. Decker, and Charles A. Jungreis for a shape memory polymer actuator and catheter provides the following state of technology information, "An actuator system is provided for acting upon a material in a vessel. The system includes an optical fiber and a shape memory polymer material operatively connected to the optical fiber. The shape memory polymer material is adapted to move from a first shape for moving through said vessel to a second shape where it can act upon said material." (Abstract)

United States Patent Application No. 2003/0236533 by Thomas S. Wilson, Duncan Maitland, Daniel L. Schumann, Steve L. Little, and Paul E. Ahre for a Shape Memory Polymer Actuator and Catheter provides the following state of technology information, "A system for removing an occlusion from a vessel. The system utilizes a shape memory polymer device for acting upon the occlusion. A transport vehicle moves a shape memory material through the vessel. The shape memory material is adapted to move from a first unexpanded coil shape to move through or around the occlusion, to a second expanded coil shape for acting upon the occlusion. A heat transfer mechanism is operatively connected to the shape memory material and is adapted to transfer heat to the shape memory material to move the shape memory material from the first shape to the second shape. The transport vehicle and the shape memory polymer material are withdrawn through the conduit carrying the occlusion matter.

The system may include a second shape memory polymer device situated so that the occlusion material is gripped from both sides to facilitate removal." (Abstract)

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system utilizing a shape memory material with integrated actuation using embedded particles. One embodiment of the present invention provides a shape memory material apparatus comprising a shape memory material body and magnetic pieces in the shape memory material body. Another embodiment of the present invention provides a shape memory material apparatus comprising shape memory material body means for being formed in a specific primary shape, reformed into a secondary stable shape, and controllably actuated to recover the specific primary shape, and magnetic piece means in the shape memory material body means for allowing the shape memory material body means to be controllably actuated to recover the specific primary shape. Another embodiment of the present invention provides a method of actuating a device to perform an activity on a subject comprising the steps of positioning a shape memory material body in a desired position with regard to the subject, the shape memory material body capable of being formed in a specific primary shape, reformed into a secondary stable shape, and controllably actuated to recover the specific primary shape; including pieces in the shape memory material body; and actuating the shape memory material body using the pieces causing the shape memory material body to be controllably actuated to recover the specific primary shape and perform the activity on the subject.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Shape materials can be formed into a specific primary shape and reformed into a secondary stable shape. The material can be controllably actuated by heating so they recover their primary shape. By embedding magnetic particles into material it becomes possible to heat and thus actuate a device remotely, with out any physical connections, using inductive heating. With appropriately sized ferromagnetic particles hysteresis losses are the major contributing mechanism of inductive heating, instead of eddy current heating, and thus it becomes possible to control the maximum temperature achieved by the particles by controlling the particles curie temperature, this allows for an automatic thermoregulation of the device and also allows controlled actuation of the device. It may also be useful in some instances to use magnetic particles which heat via an eddy current mechanism. Such particles have a greater possible heat production capability but do not have the useful feature of an automatic thermoregulation.

Figure 1:
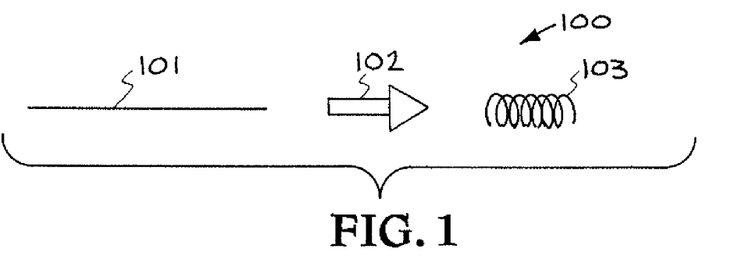
FIG. 1 illustrates an embodiment of the present invention.

The present invention provides a system utilizing a shape memory material with integrated actuation using embedded particles. Referring now to FIG. 1, an embodiment of the present invention is illustrated. The system is designated generally by the reference numeral 100. The device 100 is shown in its two stages. The device, as depicted in 101 is in its un-actuated state and the device, as depicted in 103 is in its actuated state. The un-actuated device, 101 is activated by induction heating 102.

Inductive heating and subsequent actuation of devices may be multiplexed, using different frequencies of field or different energy sources tuned to actuate different actuators or different parts of one actuator. For example, inductive heating may actuate one actuator and laser energy may actuate a second with either actuator not affected by the other energy source. Many energy sources such as ultrasound, light, RF, microwave and other electromagnetic fields may be tuned to specifically actuate single or groups of actuators. As illustrated by 102, induction heating is used to heat ferromagnetic particles imbedded in the device 100 which actuates the device.

The device has medical and other uses. For example, U.S. Pat. No. 5,895,398 to Jeffrey P. Wensel and Y. Pierre Gobin, issued Apr. 20, 1999, shows a clot capture coil. The clot capture coil is made out of a solid elastic or superelastic material which has shape memory, preferably nitinol. The elasticity or superelasticity of the coil allows it to be deformed within the catheter and to then reform its original coil configuration when the coil is moved outside of the catheter lumen. U.S. Pat. No. 5,895,398 is incorporated herein by reference.

Figure 2:
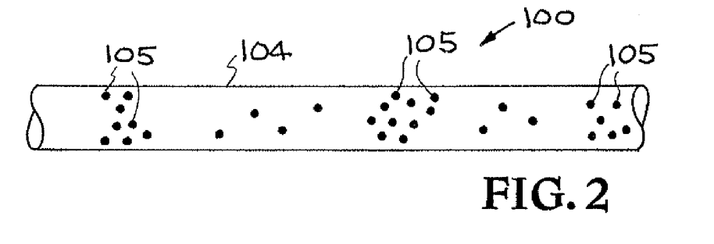
FIG. 2 is an enlarged view of a section of the device shown in FIG. 1.

Referring now to FIG. 2, an enlarged view of a section of the device 100 is shown. In one embodiment of the device 100, a Shape Memory Polymer (SMP) material 104 forms the body of the device 100. Magnetic particles 105 are embedded in the SMP material 104. In one embodiment of the device 100, the magnetic particles 105 are ferromagnetic heating particles.

The shape-memory materials, such as the material 104, have the useful ability of being formable into a primary shape, being reformable into a stable secondary shape, and then being controllably actuated to recover their primary shape. Both metal alloys and polymeric materials can have shape memory. In the case of metals, the shape-memory effect arises from thermally induced solid phase transformations in which the lattice structure of the atoms changes, resulting in macroscopic changes in modulus and dimensions. In the case of polymeric materials, the primary shape is obtained after processing and fixed by physical structures or chemical crosslinking.

The secondary shape is obtained by deforming the material while it is in an elastomeric state and that shape is fixed in one of several ways including cooling the polymer below a crystalline, liquid crystalline, or glass transition temperature; by inducing additional covalent or ionic crosslinking, etc. While in the secondary shape some or all of the polymer chains are perturbed from their equilibrium random walk conformation, having a certain degree of bulk orientation. The oriented chains have a certain potential energy, due to their decreased entropy, which provides the driving force for the shape recovery. However, they do not spontaneously recover due to either kinetic effects (if below their lower Tg) or physical restraints (physical or chemical crosslinks). Actuation then occurs for the recovery to the primary shape by removing that restraint, e.g., heating the polymer above its glass transition or melting temperature, removing ionic or covalent crosslinks, etc, Particle Material—There are a number of particle materials that can be used in this invention. A number of materials with low curie temperatures (40-100 degrees Celsius) are well suited. These materials include Ni—Si, Fe—Pt, and Ni—Pd alloys. A number of magnetic powders can be used including Ni—Zn—Fe—O, Ba—Co—Fe—O, and Fe—O. Another material is a substituted magnetite or ferric oxide crystalline lattice with a portion of the iron atoms substituted by one of the following, cobalt, nickel, manganese, zinc, magnesium, copper, chromium, cadmium, or gallium. A Palladium Cobalt alloy that also has a controllable curie temperature in the range of 40-100 degrees Celsius can also be used. Nickel Zinc Ferrite (a soft ferrite) can also be used. A very useful property of this material is that its curie temperature can be greatly influenced by the amount of Zinc present in the material. Curie temperatures ranging from 30-600 degrees Celsius are achievable [Strontium Ferrite (a hard ferrite) and Nickel (an elemental ferromagnetic material) can be used as heating particulates. These materials were calculated to produce heating rates of 1 degree Celsius per second in a field in which Nickel Ferrite was estimated to produce 50 degrees Celsius per second.

Particle Size Range—The particle sizes are only limited by there impact on the mechanical properties of desired device. Particles in the size range of 1 nm to 500 microns are used in various embodiments of the device.

The concepts of "Medical Inductive Heating" and "Thermoregulation and the Curie Temperature" provide helpful background in understanding the operation of the system 100.

As described above, embodiments of the device 100 comprise a Shape Memory Polymer (SMP) material 104 that forms the body of the device 100 with ferromagnetic heating particles 105 embedded in the SMP material 104.

Medical Inductive Heating—Inductive heating has applications in the field of Hyperthermia. Hyperthermia is a form of treatment that attempts to kill cancerous tissue by heating. Thermal seeds, magnetic material, in the form of cylindrical rods or particles are implanted in the cancerous area and are then heated using an alternating magnetic field. Field strengths, frequencies and achievable heating rates using inductive heating in the body have been analyzed. Because the temperature range desired for hyperthermia treatment and SMP actuation overlap, hyperthermia attempts to generate temperatures $\geq 42°$ C. [1] and most SMP devices can be actuated in the temperature range of $35°$ C.$\leq T \leq 80°$ C.

Thermoregulation and the Curie Temperature—A key aspect of both hyperthermia and inductively actuated SMP is thermoregulation. It is important to be able to set the maximum temperature of a heating device placed inside the body. This is important because excessive heating can damage body tissue and if it occurs in an SMP device could cause melting of the plastic, an event that would most likely have adverse effects on health. Limiting the maximum achievable temperature can be achieved with complicated and invasive feed back circuits but the simplest and most effective way of setting a maximum temperature with inductive heating is by controlling the heating materials Curie temperature (Tc) and keeping heating particles small enough so that the major mode of heating is via hysteresis loss. The Tc of a material is the temperature at which a ferromagnetic material transitions to a paramagnetic material. At Tc the materials magnetic permeability drops to that of free space and the material no longer experiences hysteresis losses. This transition is an automatic temperature control built into the heating particles. Field frequencies and strengths will not influence the Curie temperature.

The optimum material for the heating the particles is an aspect of the present invention. A number of materials with low curie temperatures (40-100 degrees Celsius) are available. These materials include Ni—Si, Fe—Pt, and Ni—Pd alloys. Also available are a number of magnetic powders and magnetic fluids including Ni—Zn—Fe—O, Ba—Co—Fe—O, and Fe—O. There is also a material that is a substituted magnetite or ferric oxide crystalline lattice with a portion of the iron atoms substituted by one of the following, cobalt, nickel, manganese, zinc, magnesium, copper, chromium, cadmium, or gallium.

Medically Safe Magnetic Field Limits—At increasing field frequencies and strengths eddy current heating can be generated in body tissues. This safety concern places limits on field strengths and frequencies that can be used in medical applications.

A simple model of heat production per unit volume tissue will be described. Simplifying a body torso to a cylinder it can be derived that $P = \sigma_t (\pi \mu_o)^2 (H_o f)^2 r^2$ where P=heat production per unit volume tissue (W/m$^3$), $\sigma_t$=electrical conductivity of the cylinder (1/$\Omega \cdot$m), $\mu_o$=magnetic permeability of free space (, $H_o$=magnetic field amplitude (A/m), f=field frequency (Hz), and r=radius from center of cylinder (m).

It becomes apparent from this equation that the heating produced in the tissue is proportional to the square of the product, $H_o f$ and r. This means that tissue farthest from the center axis of the body would be subjected to the greatest heating rates. Field intensities of 35.8 A/m at a frequency of 13.56 MHz can be tolerated for an extended period of time. A safety limit of $H_o f \leq 4.85 \times 10^8$ A·turns/m·s for whole body exposure is recommended. Field strengths and be increased for extremities, such as the head or the arms since these portions of the body have smaller radii. The device 100 should be operated at the correct frequency and magnitude magnetic field.

The device 100 can be used in a number of fields ranging from medical to manufacturing. There are numerous benefits and applications of the system 100. Firstly there is the benefit that the material has a built in actuation mechanism. This is beneficial because it will simplify designs of SMP devices. Even and consistent heating through the entire SMP material will be achieved with out the need to design laser heating or resistive heating elements. Secondly, the system 100 is particularly useful in applications where it is difficult to supply a physical energy connection to a SMP device. SMP surgical devices that are delivered via catheters or minimally invasive tools are good examples of such an application. The space saving from eliminating optical fibers or wires needed to actuate SMP surgical devices will allow new medical devices, made from the inductively actuated SMP to reach smaller and narrower vascular passageways creating possibilities for new life saving devices and techniques.

The system 100 provides an actuator activated by heating via an inductively created magnetic field. Induction heating is used to heat ferromagnetic particles imbedded in a Shape Memory Polymer which in turn actuates the device.

Figure 3:
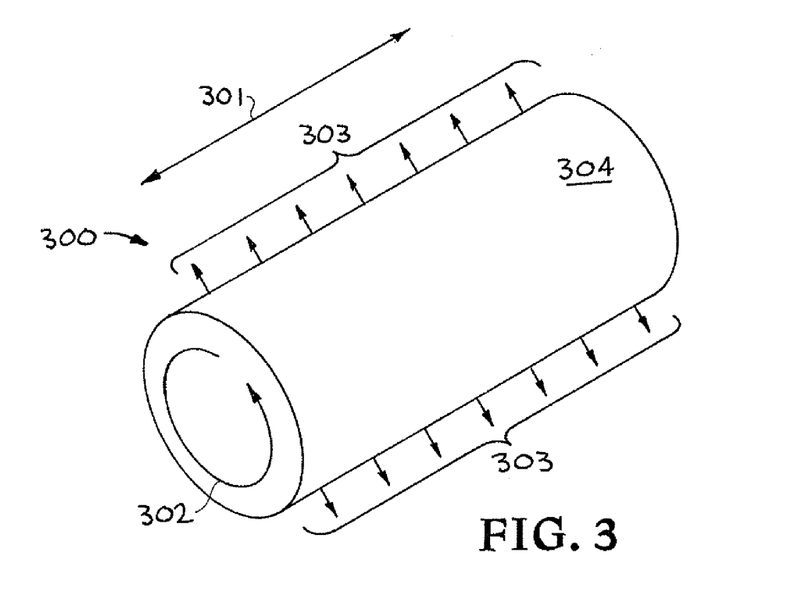
FIG. 3 is an enlarged view of a heating element/particle.
Figure 7:
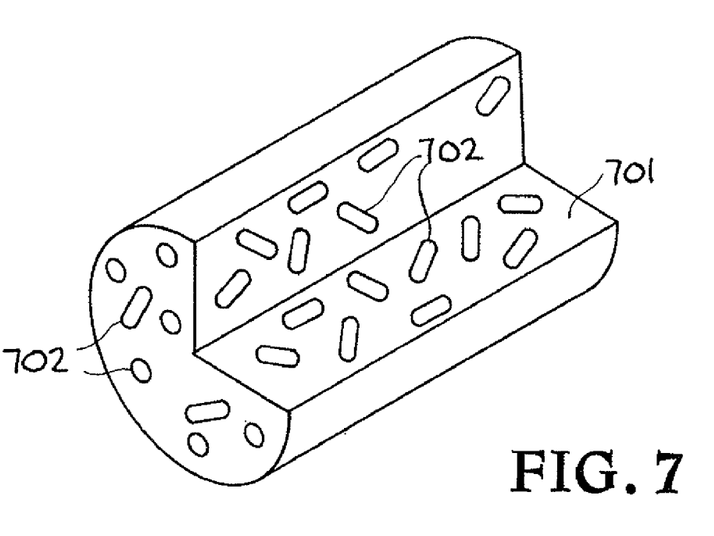
FIG. 7 illustrates another embodiment of the present invention.
Figure 8:
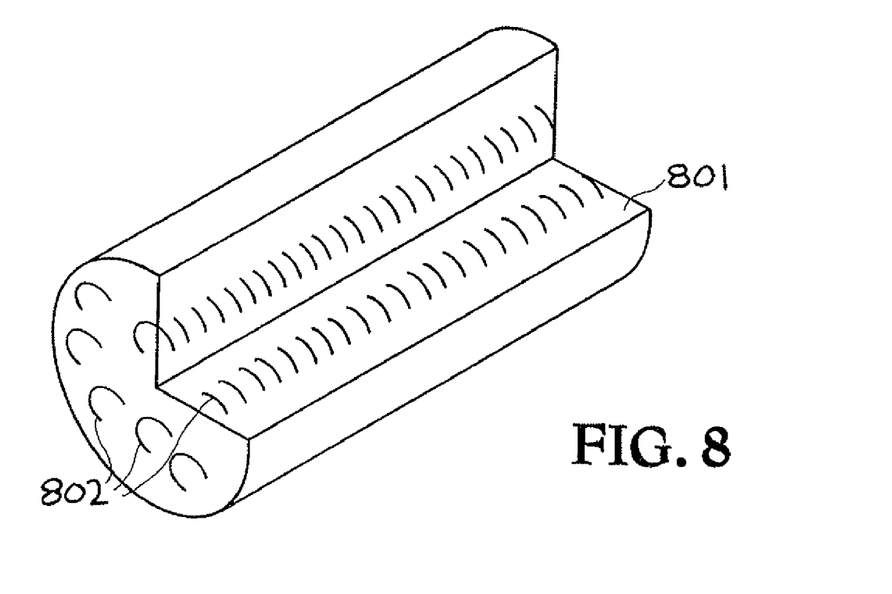
FIG. 8 illustrates another embodiment of the present invention.
Figure 9:
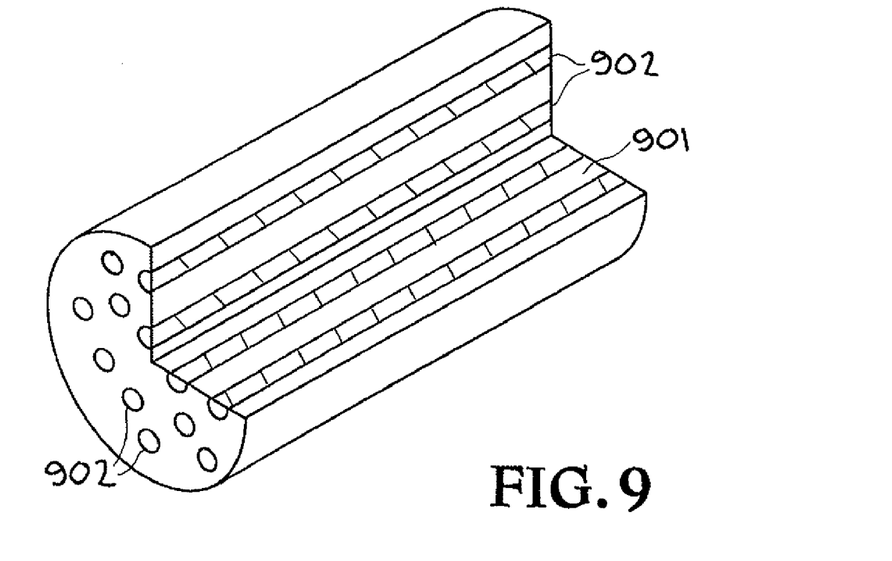
FIG. 9 illustrates another embodiment of the present invention.

Referring now to FIG. 3 another embodiment of the present invention is illustrated. This embodiment is designated generally by the reference numeral 300. The embodiment 300 illustrates a close up of a heating element undergoing a mode of inductive heating known as eddy current heating. This mode of inductive heating allows the heating elements to take the form of particles as demonstrated in FIG. 2, cylindrical rods as demonstrated in FIG. 7 (702) and FIG. 8 (802), or spring coil shapes as demonstrated in FIG. 9 (902). Eddy current heating is where alternating magnetic fields are used to induce electrons to flow in a material which in turn generates heat due to the electrical resistance of the material. This differs from hysteresis loss heating which is generated due to a thermodynamically irreversible process that occurs in a ferromagnetic material when the magnetic orientation of the material is reversed. These two modes of heating, hysteresis loss and eddy current loss are fundamentally different. An eddy current mode of heating is capable of producing a greater amount of heat then hysteresis modes of heating, however eddy current heating has the disadvantage of not having a mechanism of curie temperature thermoregulation. Meaning it is not as easy to control the maximum temperature of the heating particles using elements which heat via an eddy current mode. In FIG. 3 the direction of the alternating magnetic field is designated by the reference numeral 301. The induced electrical current is designated by the reference numeral 302. Heat 303 is emitted from the central body 304. The heat can be calculated by the formula: $P=I\_R$, where P=Power, I=Current (Amps), and R=Electrical Resistance (Ÿ).

Figure 6:
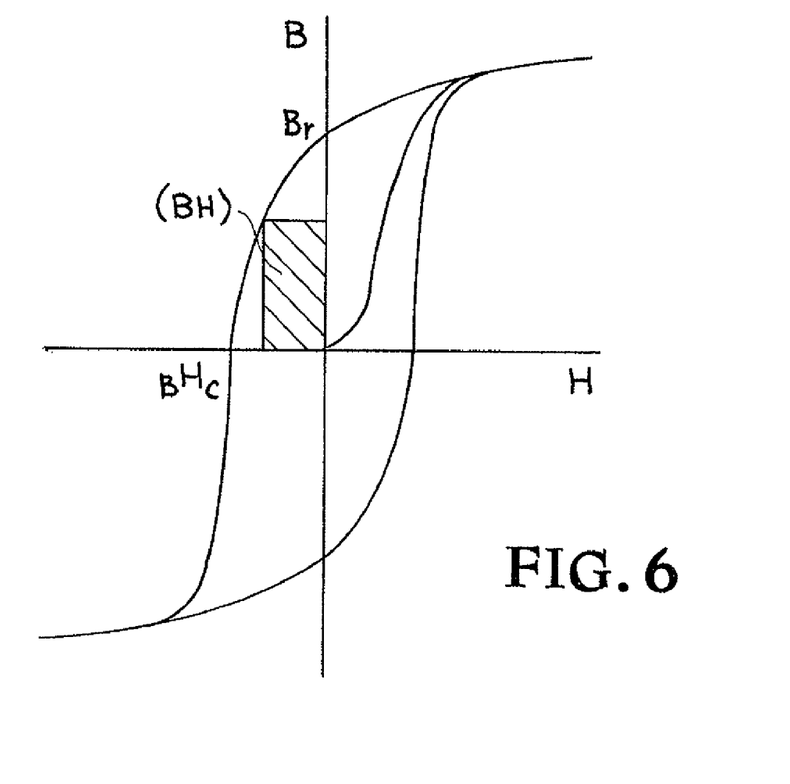
FIG. 6 illustrates the hysteresis loss mode of heating.

Another embodiment of the invention is the use of heating elements that are heated inductively via a hysteresis loss mechanism. Magnetic hysteresis is due to a thermodynamically irreversible process that occurs in a ferromagnetic material when the magnetic orientation of the material is reversed. The amount of heating produced by hysteresis losses is a function of the shape of the materials hysteresis loop which is determined by the materials microstructure, physical and processing characteristics and by the field frequency and strength the material is subjected to. A general form of a hysteresis loop is illustrated in FIG. 6. A wide square hysteresis loop is most desirable for a heating element because the area inside the hysteresis loop is equal to the amount of energy dissipated as heat. In order to maintain the thermo-physical properties of the SMP, and ensure the heating mode of the particles is hysteresis loss nano and micrometer sized particles should be used. Due to the small size of these particles any eddy currents that are generated are very small and would not contribute significantly to heating allowing the thermoregulation of the particles to be dictated by the Curie temperature.

Figure 4:
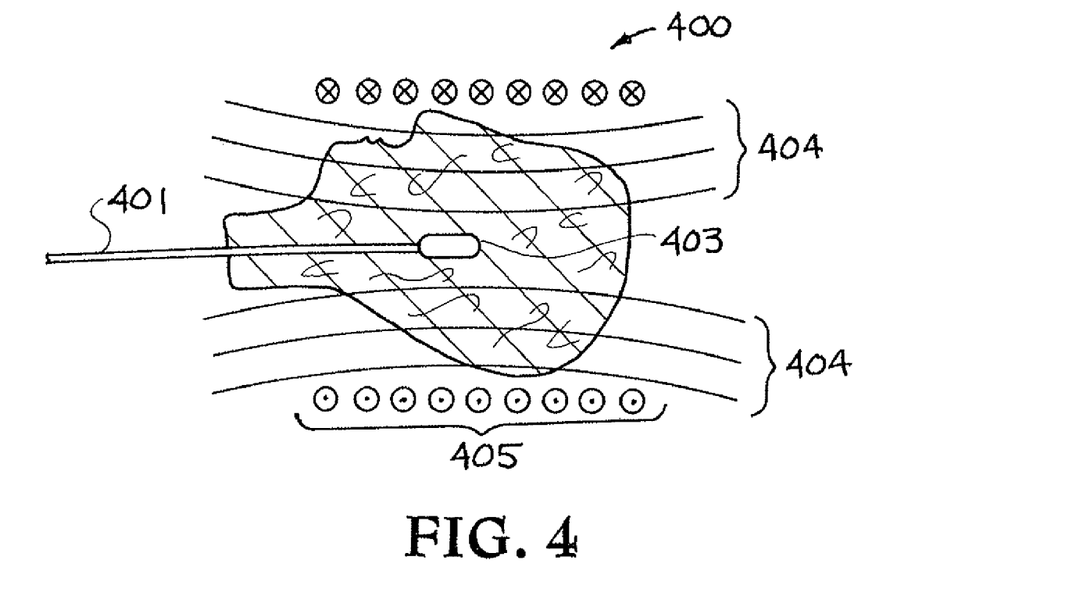
FIG. 4 illustrates another embodiment of the present invention.

Referring now to FIG. 4, another embodiment of the present invention is illustrated. The system is designated generally by the reference numeral 400. An actuator 403 is carried by a catheter 401. The catheter 401 and actuator 403 are shown inside a patient 402. An inductive coil 405 is located outside the body 402 creating magnetic field lines 404. The actuator 403 acts on the patient 402 through the inductive coil 405 that activates the actuator 403.

The system 400 provides a method of actuating a device in order to perform an activity on a subject such as the patient 402. The subject can also be an animal or other subject. A shape memory material body is formed in a specific primary shape, reformed into a secondary stable shape, controllably actuated to recover the specific primary shape, and located in a desired position with regard to the subject. The shape memory material body is controllably actuated causing it to recover said specific primary shape and perform the activity on the subject. Some examples of activities that can be performed on a subject are described in the following patents; however, there are other activities that can be performed on a subject. U.S. Pat. No. 5,895,398 shows a method of using a clot capture coil. U.S. Pat. No. 5,911,737 shows microfabricated therapeutic actuators. U.S. Pat. No. 6,059,815 shows microfabricated therapeutic actuators. U.S. Pat. No. 6,102,917 shows a system for releasing a target material, such as an embolic coil from an SMP located at the end of a catheter utilizing an optical arrangement for releasing the material. United States Patent Application No. 2002/0095169 shows a shape memory polymer actuator and catheter for acting upon a material in a vessel. United States Patent Application No. 2003/0236533 shows a shape memory polymer actuator and catheter for removing an occlusion from a vessel. The patents and the patent application are incorporated herein by reference.

In various embodiments of the invention methods are provided for actuating a device to perform an activity on a subject. The various embodiments comprise the steps of positioning a shape memory material body in a desired position with regard to the subject, the shape memory material body capable of being formed in a specific primary shape, reformed into a secondary stable shape, and controllably actuated to recover the specific primary shape; including pieces in the shape memory material body; and actuating the shape memory material body using the pieces causing the shape memory material body to be controllably actuated to recover the specific primary shape and perform the activity on the subject. One embodiment includes using pieces which heat via a hysteresis loss mode and has a Curie temperature (Tc) wherein the Tc of the pieces is the temperature at which a ferromagnetic material transitions to a paramagnetic material. Another embodiment uses pieces which heat via a hysteresis loss mode having controllable curie temperature in the range of 40-100 degrees Celsius. Another embodiment uses pieces which heat via an eddy current mode. Another embodiment includes the steps of controllably heating and thus actuating the shape memory material body by heating the pieces using an alternating magnetic field. Another embodiment includes the steps of controllably actuating the shape memory material body by heating the pieces using an externally applied magnetic field. Another embodiment includes the steps of controllably actuating the shape memory material body by heating the pieces using ultrasound. Another embodiment includes the steps of controllably actuating the shape memory material body by heating the pieces using microwaves. Another embodiment includes the steps of controllably actuating the shape memory material body by heating the pieces using light. Another embodiment includes the steps of controllably actuating the shape memory material body by heating the magnetic pieces using RF.

Figure 5:
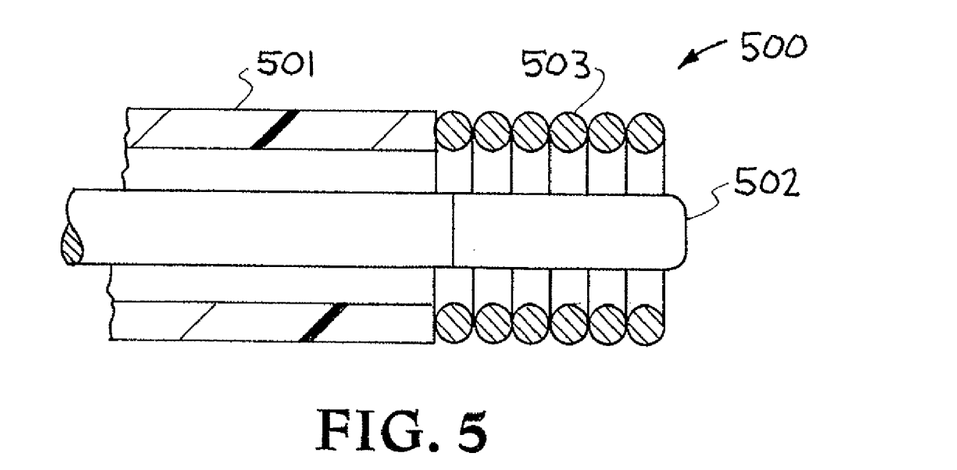
FIG. 5 illustrates another embodiment of the present invention.

Referring now to FIG. 5, another embodiment of the present invention is illustrated. The embodiment is designated generally by the reference numeral 500. An actuator 502 is carried by a catheter 501. A miniature inductive coil 503 is carried by a catheter 501. The actuator 502 can be inside or acting on a patient with the miniature inductive coil 503 near the actuator 502.

Field Frequency and Magnitude Range for Medical Applications—At increasing field frequencies and strengths eddy current heating can be generated in body tissues. This safety concern places limits on field strengths and frequencies that can be used in medical applications. Simplifying a body torso to a cylinder one derives that $P=\sigma_f(\pi\mu_o)^2(H_o f)^2 r^2$ where P=heat production per unit volume tissue (W/m³), $\sigma_f$=electrical conductivity of the cylinder (1/Ω·m), $\mu_o$=magnetic permeability of free space 0, $H_o$=magnetic field amplitude (A/m), f=field frequency (Hz), and r=radius from center of cylinder (m). It becomes apparent from this equation that the heating produced in the tissue is proportional to the square of the product, $H_o f$ and r. This means that tissue farthest from the center axis of the body would be subjected to the greatest heating rates. This being known Atkinson, Brezovich, and Chakraborty conducted experiments with numerous people and found that field intensities of 35.8 A/m at a frequency of 13.56 MHz could be tolerated for an extended period of time. They developed a safety limit of $H_o f \leq 4.85 \times 10^8$ A·turns/m·s for whole body exposure. It was also pointed out that field strengths could be increased for extremities, such as the head or the arms since these portions of the body have smaller radii.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A shape memory material apparatus for performing an activity on a patient, comprising:
   a catheter adapted to be positioned to perform an activity on a patient,
   an actuator carried by said catheter,
   said actuator including a shape memory material body, wherein said shape memory material body comprises a shape memory material, wherein said shape memory material body comprises a polymeric material or a metal alloy material, and
   magnetic pieces in said shape memory material body, said magnetic pieces being Ni—Zn—Fe—O magnetic materials.

2. The shape memory material apparatus of claim 1 wherein said shape memory material body comprises a material having a Curie temperature (Tc) wherein said Tc of said material is the temperature at which a ferromagnetic material transitions to a paramagnetic material.

3. The shape memory material apparatus of claim 1 wherein said shape memory material body comprises a Ni—Si alloy.

4. The shape memory material apparatus of claim 1 wherein said shape memory material body comprises a Fe—Pt alloy.

5. The shape memory material apparatus of claim 1 wherein said shape memory material body comprises a Ni—Pd alloy.

6. The shape memory material apparatus of claim 1 wherein said shape memory material body comprises a Ba—Co—Fe—O magnetic powder or magnetic fluid.

7. The shape memory material apparatus of claim 1 wherein said shape memory material body comprises a Fe—O magnetic powder or magnetic fluid.

8. The shape memory material apparatus of claim 1 wherein said shape memory material body comprises a magnetite or ferric oxide crystalline lattice with a portion of the iron atoms substituted by one of the following, cobalt, nickel, manganese, zinc, magnesium, copper, chromium, cadmium, or gallium.

9. The shape memory material apparatus of claim 1 wherein said magnetic pieces comprise embedded magnetic particles.

10. The shape memory material apparatus of claim 1 wherein said magnetic pieces comprise ferromagnetic heating particles.

11. The shape memory material apparatus of claim 1 wherein said magnetic pieces comprise a material with a low curie temperature.

12. The shape memory material apparatus of claim 1 wherein said magnetic pieces comprise a material with a low curie temperature in the range of 40-100 degrees Celsius.

13. The shape memory material apparatus of claim 1 wherein said magnetic pieces comprise a Ni—Si alloy.

14. The shape memory material apparatus of claim 1 wherein said magnetic pieces comprise a Fe—Pt alloy.

15. The shape memory material apparatus of claim 1 wherein said magnetic pieces comprise a Ni—Pd alloy.

16. The shape memory material apparatus of claim 1 wherein said magnetic pieces comprise a Ba—Co—Fe—O magnetic powder.

17. The shape memory material apparatus of claim 1 wherein said magnetic pieces comprise a Fe—O magnetic powder.

18. The shape memory material apparatus of claim 1 wherein said magnetic pieces comprise a substituted magnetite or ferric oxide crystalline lattice with a portion of the iron atoms substituted by one of the following, cobalt, nickel, manganese, zinc, magnesium, copper, chromium, cadmium, or gallium.

19. The shape memory material apparatus of claim 1 wherein said magnetic pieces comprise a Palladium Cobalt alloy.

20. The shape memory material apparatus of claim 1 wherein said magnetic pieces comprise a Palladium Cobalt alloy that has a controllable curie temperature in the range of 40-100 degrees Celsius.

21. The shape memory material apparatus of claim 1 wherein said magnetic pieces comprise particles having a size range of 1 nm to 500 microns.

22. The shape memory material apparatus of claim 1 wherein said magnetic pieces comprise magnetic rods.

23. The shape memory material apparatus of claim 1 wherein said magnetic pieces comprise cylindrical magnetic rods.

24. The shape memory material apparatus of claim 1 wherein said magnetic pieces comprise magnetic rods of a material with a low curie temperature in the range of 40-100 degrees Celsius.

25. The shape memory material apparatus of claim 1 including apparatus for controllably actuating said shape memory material body.

26. The shape memory material apparatus of claim 1 including apparatus for controllably actuating said shape memory material body by heating said body using light.

27. The shape memory material apparatus of claim 1 including a catheter.

28. The shape memory material apparatus of claim 1 including a miniature inductive coil.

29. A shape memory material apparatus, comprising:
a shape memory material body adapted to be formed in a specific primary shape, reformed into a secondary stable shape and controllable actuated to recover said specific primary shape, wherein said shape memory material body is a Ba—Co—Fe—O magnetic powder or magnetic fluid, and
magnetic pieces in said shape memory material body, said magnetic pieces adapted to be controllably actuated to enable said shape memory material body to recover said specific primary shape.

30. A shape memory material apparatus, comprising:
a shape memory material body adapted to be formed in a specific primary shape, reformed into a secondary stable shape, and controllably actuated to recover said specific primary shape, wherein said shape memory material body means is a Fe—O magnetic powder or magnetic fluid, and
magnetic pieces in said shape memory material body, said magnetic pieces adapted to be controllably actuated to enable said shape memory material body to recover said specific primary shape.

31. A shape memory material apparatus, comprising:
a shape memory material body adapted to be formed in a specific primary shape, reformed into a secondary stable shape, and controllably actuated to recover said specific primary shape, wherein said shape memory material body means is a magnetite or ferric oxide crystalline lattice with a portion of the iron atoms substituted by one of the following, cobalt, nickel, manganese, zinc, magnesium, copper, chromium, cadmium, or gallium, and
magnetic pieces in said shape memory material body, said magnetic pieces adapted to be controllably actuated to enable said shape memory material body to recover said specific primary shape.

32. A shape memory material apparatus, comprising:
a shape memory material body adapted to be formed in a specific primary shape, reformed into a secondary stable shape, and controllably actuated to recover said specific primary shape, and
magnetic pieces in said shape memory material body, said magnetic pieces adapted to be controllably actuated to enable said shape memory material body to recover said specific primary shape wherein said magnetic pieces comprise a Ba—Co—Fe—O magnetic powder.

33. A shape memory material apparatus, comprising:
a shape memory material body adapted to be formed in a specific primary shape, reformed into a secondary stable shape, and controllably actuated to recover said specific primary shape, and
magnetic pieces in said shape memory material body, said magnetic pieces adapted to be controllably actuated to enable said shape memory material body to recover said specific primary shape wherein said magnetic pieces comprise a Fe—O magnetic powder.

34. A shape memory material apparatus, comprising:
a shape memory material body adapted to be formed in a specific primary shape, reformed into a secondary stable shape, and controllably actuated to recover said specific primary shape, and
magnetic pieces in said shape memory material body, said magnetic pieces adapted to be controllably actuated to enable said shape memory material body to recover said specific primary shape wherein said magnetic pieces comprises a substituted magnetite or ferric oxide crystalline lattice with a portion of the iron atoms substituted by one of the following, cobalt, nickel, manganese, zinc, magnesium, copper, chromium, cadmium, or gallium.

* * * * *